United States Patent
Arisawa et al.

(10) Patent No.: US 6,906,283 B2
(45) Date of Patent: Jun. 14, 2005

(54) METHOD OF PROCESSING SUBSTANCES BY SHORT-PULSE, WAVELENGTH TUNABLE RAMAN LASER

(75) Inventors: Takashi Arisawa, Kyoto (JP); Kyoichi Deki, Kyoto (JP); Fumiaki Matsuoka, Kyoto (JP)

(73) Assignee: Japan Atomic Energy Research Institute, Tokyo (JP)

( * ) Notice: Subject to any disclaimer, the term of this patent is extended or adjusted under 35 U.S.C. 154(b) by 464 days.

(21) Appl. No.: 09/985,022

(22) Filed: Nov. 1, 2001

(65) Prior Publication Data
US 2002/0172234 A1 Nov. 21, 2002

(30) Foreign Application Priority Data
Mar. 16, 2001 (JP) ......................................... 2001-076026

(51) Int. Cl.[7] ............................................... B23K 26/00
(52) U.S. Cl. ................................ 219/121.85; 219/121.6
(58) Field of Search ........................... 219/121.85, 121.6

(56) References Cited

U.S. PATENT DOCUMENTS

| 4,907,586 | A | * | 3/1990 | Bille et al. ...................... 606/5 |
| 6,070,093 | A | * | 5/2000 | Oosta et al. .................. 600/316 |
| 6,156,030 | A | * | 12/2000 | Neev ............................. 606/10 |
| 6,340,806 | B1 | * | 1/2002 | Smart et al. ........... 219/121.62 |

* cited by examiner

Primary Examiner—M. Alexandra Elve
(74) Attorney, Agent, or Firm—Banner & Witcoff, Ltd.

(57) ABSTRACT

Short-pulse Raman laser is used to perform precision working of a substance without causing thermal effects on it or examine the interior of the skin or process the interior of a transparent material such as glass. By typically choosing a suitable Raman medium to be illuminated with a pump laser, the short-pulse Raman laser can have a wavelength that matches the wavelength of absorption by the substance of interest.

5 Claims, 6 Drawing Sheets (4 of 6 Drawing Sheet(s) Filed in Color)

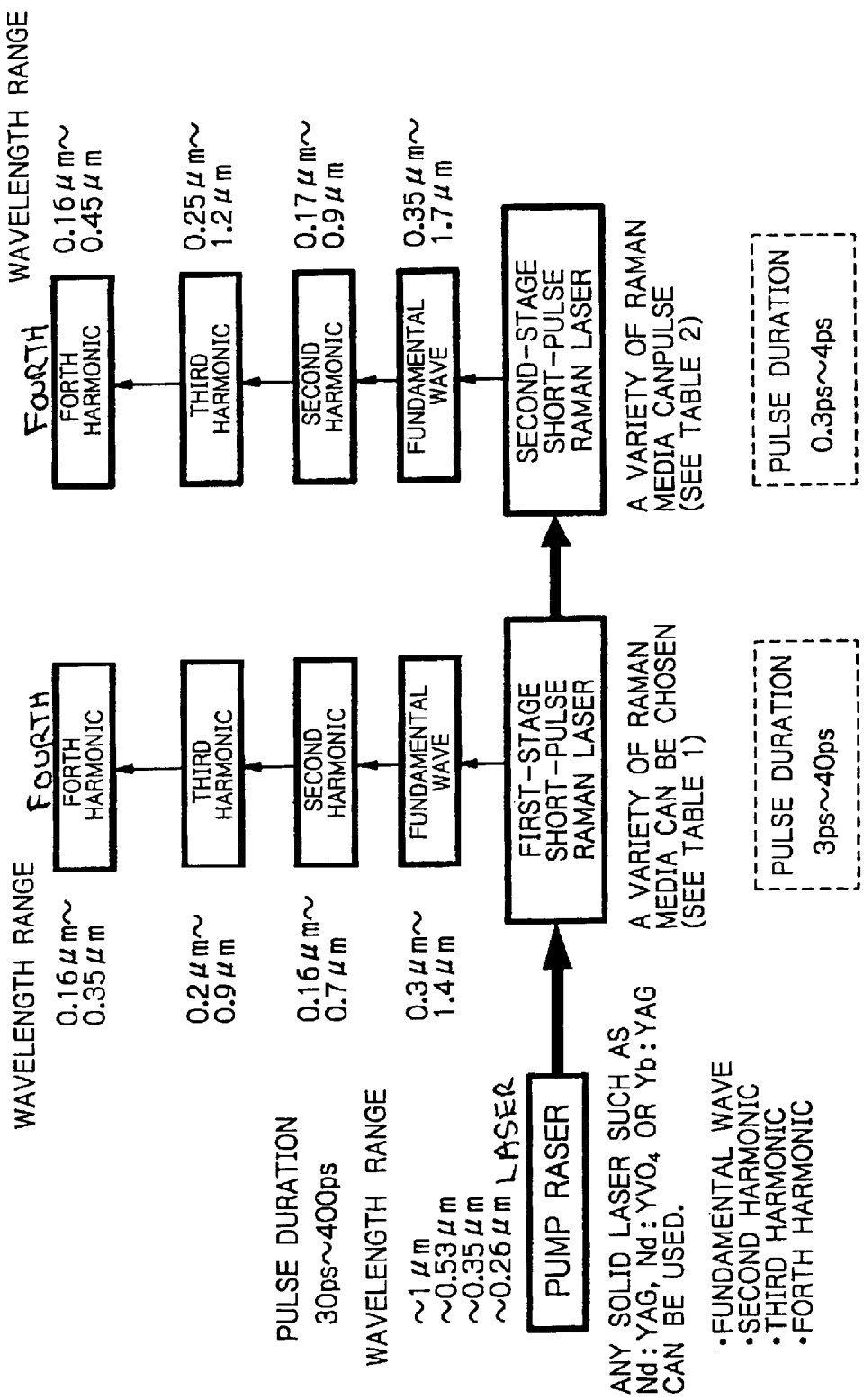

SURFACE PROCESSING (WITH LONG PULSES)

SURFACE PROCESSING (WITH LONG PULSES)

SURFACE PROCESSING (WITH SHORT PULSES)

SURFACE PROCESSING (WITH SHORT PULSES)

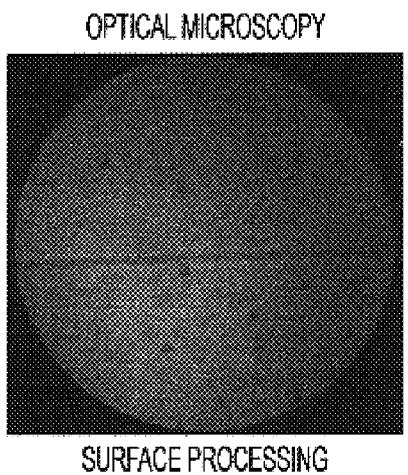
FIG. 5A — SURFACE PROCESSING (WITH SHORT PULSES)
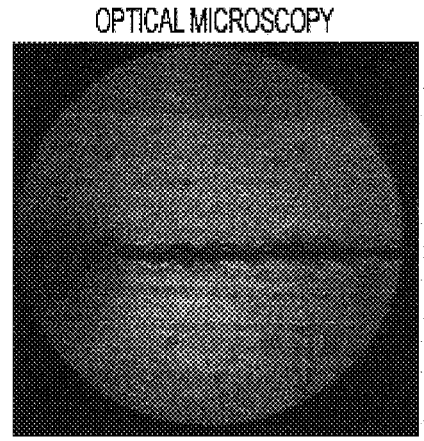
FIG. 5B — INTERNAL PROCESSING (WITH SHORT PULSES)

GLASS

SILICON

METHOD OF PROCESSING SUBSTANCES BY SHORT-PULSE, WAVELENGTH TUNABLE RAMAN LASER

This application is based upon and claims the benefit of priority from Japanese Patent Application No. 76026/2001, filed Mar. 16, 2001, the entire contents of this application are incorporated herein by reference.

BACKGROUND OF THE INVENTION

This invention relates to a method in which short-pulse laser light having an absorption wavelength matching the optical characteristics of a substance to be processed or measured is used to process the surface or interior of the substance with high efficiency and precision but without producing any thermal effects, cracks and other unwanted phenomena in the substance. Typically, this invention finds specific use in the surface or thin-film processing technology, or in the technology of processing the surface or interior of transparent substances such as glass, or in medical technology for examining the sub-surface area of living tissues.

In the invention, short-pulse Raman laser light is used as short-pulse laser light and this offers an advantage in that the wavelength or pulse duration which match laser light absorption by the substance of interest can be varied easily and in a compact way such as by varying the Raman medium, changing the Raman pump laser wavelength, or using harmonics of Raman light.

In the invention, laser light is concentrated and condensed as much as possible to provide high enough luminance in processing and measurement. In order to ensure that light is concentrated on the substance of interest with high enough intensity, the quality of laser beam has conventionally been improved to achieve spatial concentration. In the present invention, the degree of laser light's concentration is enhanced as an overall value that is expressed by (temporal concentration)×(spatial concentration)×(wavelength-related concentration). Temporal concentration is achieved by short pulses whose duration ranges from the sub-pico to pico second order; spatial concentration is achieved by the good spatial mode of Raman light; and wavelength-related concentration is achieved by allowing the substance to effect one-photon or many-photon absorption of the light in a nearly resonant manner.

By adopting this technique, the heat input to the substance of interest is limited to the smallest possible level so that efficient processing and measurement are realized by means of small laser equipment. The performance of the short-pulse Raman laser satisfies all these requirements.

Before the development of the short-pulse Raman laser, no lasers were available that satisfied the requirements for short pulse duration, high peak intensity, high repetition rate and wavelength tunability and which still were compact and capable of being used to process substances in various industrial fields. In addition, the conventional lasers have had the following problems that prevent their effective use in measurement, processing or medical treatment by adjusting optimum laser wavelength or pulse duration for the substance of interest so that no significant thermal effects will be left on the substance.

(1) In the common CPA (chirped pulse amplification) system, the laser or active medium has a broad wavelength range but the system is bulky and complex, making it necessary to precisely adjust the pulse waveform, spatial mode, polarization, dispersion and other factors of laser beam. As a result, the wavelength and pulse duration of laser light are difficult to alter in a desired way and prolonged laser operation is also difficult.

(2) In OPA (optical parametric amplification), amplification is achieved by white, short-pulse laser light from a wavelength-tunable short-pulse laser; however, it generates only insufficient pulse energy to be useful in processing, measurement and medical treatment.

Hence, the effort to apply the conventional lasers to short-pulse laser processing has involved the following problems. If processing is performed with an amplified Ti sapphire laser, adequate intensity is obtained but due to the limited oscillating frequency, it is difficult to achieve resonance, or frequency match with the absorption band for the substance of interest. If there is no match with the absorption band, processing requires far more intense pulses than are required when resonance is achieved and the leading edge of a pulse first generates an intense Stark spread in the substance and an ensuing pulse causes electrons to be driven by the electric field of the laser.

As a result, many-photon absorption occurs to create a high-energy state and a multi-valent ion plasma develops to break down the substance by the coulomb force, leading to ablation. If the energy of the absorption band is small (i.e. the wavelength is long), the absorption of a single photon is sufficient to achieve processing as expressed by the following relations:

$$\Delta E \sim h\nu \text{ (one photon provides near resonance)}$$

$$\Delta E \neq h\nu \text{ (one photon provides no resonance)}$$

where $\Delta E$ is the energy absorbed by the substance of interest, $\nu$ is the number of vibrations of one laser photon, and h is Planck's constant ($h\nu$: the energy of a photon).

However, if the energy of the absorption band is large (i.e. the wavelength is short), many photons have to be absorbed to achieve processing as expressed by the following relations:

$$\Delta E = nh\nu \text{ (n photons provide near resonance)}$$

$$\Delta E = nh\nu \text{ (n photons provide no resonance)}$$

In the many-photon absorption process, if the energy of the absorption band for the substance differs greatly from the many-photon wavelength of laser ($nh\nu$), the processing reaction first takes place at the point in time when laser light having an extremely high trailing edge of pulse is launched and the leading edge of the laser pulse is not used effectively. This is a serious problem since the laser light has only short pulse duration.

As just described above, if there is a great wavelength mismatch, the interaction with the substance of interest starts from the tail of the intense Stark spread at the middle stage of pulse illumination and the leading edge of the short pulse does not make any contribution to processing; this not only results in inefficient use of the laser light but also leads to the development of cracks in the substance due to unwanted light; if the processing does not cause significant thermal adverse effects, lossy heating of the substance occurs.

The only laser that can be used for measurement and processing purposes without experiencing the problems described above is the short-pulse Raman laser which has the following features.

(1) An optimum pulse duration (of the pico to sub-pico second order) that is necessary for processing can be greatly changed by simply altering the conditions for condensing light from the pump laser or the type of crystal. Raman laser pulses are generated if light is condensed to provide a shape (length) exceeding the Raman threshold and, hence, the pulse duration can be changed in an easy and compact way by adjusting focal length of the lens or the beam in the Raman medium.

(2) Wavelength can be tuned in an easy and compact way by using the following techniques either alone or in combination:

changing the type of Raman crystal to choose a suitable wavelength and pulse duration;

choosing the wavelength of the pump laser performing nonlinear transformations of Raman laser light (i.e. generating harmonics which are one half, a third, a fourth or otherwise of the initial wavelength, adding the energies of any two light beams to generate the sum frequency, or subtracting the energy of any one light beam from the energy of another light beam to generate the difference frequency), thereby permitting wavelength choice from a broad range.

(3) When performing these nonlinear transformations, Raman laser light can be obtained coaxially with the pump beam, so adjustments such as the change of Raman crystal can be easily accomplished.

(4) Raman light is generated by the nonlinear effect that occurs in areas of high optical intensity and, unlike the conventional laser medium, the Raman medium is not heated, so the desired wave plane is automatically obtained; in addition, the high-quality light produced in the oscillator is amplified by the Raman laser amplifier, so high-quality light having an intensity of at least $TW/cm^2$ which is necessary for non-thermal processing can be easily attained.

The present invention has been accomplished in order to enable the following operations to be performed in the laser-based processing or measuring technology.

(1) high-efficiency, non-thermal, fast processing or measurement using a short-pulse laser having an optimum wavelength and pulse duration for the substance of interest (this can be accomplished by a short-pulse Raman laser);

(2) processing by ultra-fine condensation of light that can be realized by the Raman laser featuring flat wave planes;

(3) micro-processing that can realize finer condensation of light than achieved by the apparent beam size since the many-photon effect is more pronounced in the center of the beam than in the other areas.

In order to attain these objects, the present inventors gathered the data described below and developed optimum techniques for spectral measurement and processing.

(1) It has been found that the processing steps evolved in the following way as the result of changing parameters such as laser intensity and pulse duration. The processing steps depend largely upon many factors including pulse duration, energy and wavelength of the laser, as well as the heat conductivity of the material.

1) Arrival of Laser Light to the Surface of the Work

The leading edge of laser pulse is not yet intense enough but upon arrival to the surface of the substance, polarization is induced on the surface of the material or surface electrons, being sensitive to the electric field of the laser, come into vigorous motion. In the absence of resonant absorption, surface reflection occurs.

2) Start of Absorption

If the material has a resonant absorption band, electrons in the outermost shell become resonantly sensitive and come into motion; the moving electrons are perturbed by the electric field of the laser which progressively grows in intensity and the process of ionization continues as the electrons repeatedly impinge on the surrounding atoms. If a wavelength is used that does not match resonant absorption, electrons in an outer shell start to move only after the pulse has acquired a strong enough intensity; in other words, the leading edge of the laser pulse is not effectively absorbed and it is necessary to use pulses having a stronger overall energy.

3) Heating in the Direction of Travel of Laser Light

The short-pulse laser has a pulse duration of the sub-pico to pico second order and applies heat by condensing the laser light over a length of the 100 $\mu$m order. As a result, compared to conventional laser working with pulse durations longer than the nano-second order, the short-pulse laser allows for the progress of sufficiently local heating to minimize the thermal effect on areas that should be left intact.

4) Effect on Electrons in Inner Shells

As its intensity increases, the influence of the applied electric field shifts from the electrons in the outermost shell to those in inner shells. Upon the first occurrence of resonant absorption, electrons are stripped off and the electric field permeates further inward. However, in the absence of resonant absorption, the laser must have more intense electric field in order to remove the electronic shield.

5) End of Electronic Drive

The laser pulses drive electrons such that they are accelerated to go further beyond the areas illuminated with the laser beam. The degree of electron's acceleration depends on the energy of the laser pulses. When the application of the laser pulses ends, thee is no applied electric field that drives electrons.

6) Heating in a Direction Perpendicular to the Direction of Laser Launching.

The energy of an electron is transferred to the lattice within a very short period of the pico second order, whereupon the temperature of the material begins to rise. When the temperature increases to the melting point of the material, the material starts to melt and when its boiling point is reached, the material evaporates, whereupon further impingement is repeated to create a plasma. The electrons accelerated into the solid undergo further impingement and not only the areas illuminated with the laser but also other areas are thermally affected. Hence, in the absence of resonant absorption, an even higher pulse energy is applied and electrons are further accelerated by the applied electric field of the laser to expand the area being heated. In this way, thermally affected areas occur around the area to be worked and this in turn contributes to the development of mechanical cracks in areas surrounding those thermally affected areas. An effective way to reduce these adversely affected areas is by concentrating the laser energy in an amount that is minimum and necessary for working the material.

7) Plasma Diffusion and Heating

High-energy electrons within the plasma impinge against atoms as they diffuse and this triggers another process of ionization. If the progress of plasma diffusion has reached a sufficient stage, cooling occurs adiabatically and recombination also occurs to effect recovery to the initial neutral atoms.

8) Cooling of Interior of the Solid

Sufficient temperature diffusion through the solid promotes the cooling process.

(2) Presence of Resonance Effect as Compared with its Absence.

Comparison is now made for the following two substances.

A) a substance in which effective absorption takes place due, for example, to the many-photon effect B) a substance in which absorption does not take place easily in the absence of the many-photon effect Considering the processing steps 1)-8), the substance A) is capable of more rapid energy absorption than B) and the laser energy is used more effectively to process the illuminated areas. On the other hand, the substance B) allows the internal electrons to be accelerated to areas beyond the areas to be worked. Therefore, it would be effective to use a wavelength-tunable laser that generates short pulses at a wavelength that can be efficiently absorbed by the material. Needless to say, the effect will become very pronounced if direct processing is performed with the short-wavelength laser. It should, however, be noted that in the absence of many-photon absorption, the surface and the interior of the material are similarly processed and it is impossible to achieve selective processing of the interior of a transparent material.

(3) Choice of Raman Medium and Generation of Harmonics for Realizing Optimum Wavelength (see Table 1)

(4) Condensing Raman Pump Laser for Realizing Optimum Pulse Duration

In the present invention, the following measures are taken to make the most of the above-described features of the short-pulse Raman laser.

1) Changing the Pulse Duration

FIG. 1 shows in the top a conventional short-pulse laser system and it shows in the bottom a Raman laser (crystal) and the theory of its oscillation. Raman laser light 1 has such a pulse duration that if the pump laser light 2 from the conventional short-pulse laser system is condensed in a Raman crystal 3, Raman light is generated within the crystal in an area exceeding the Raman threshold value and amplification occurs as backscattering (backward Raman light 4). The shortest pulse duration is limited by the phonon life. Hence, use of a short-focus optical system or a crystal of short phonon life helps generate short-pulse Raman laser light. Of course, the shortest-pulse laser cannot be made shorter than the phonon life which is inherent in the Raman crystal but longer pulses can be determined by adjusting the length of the optical system or the crystal.

2) Choice of Optimum Absorption Wavelength i) In the Case of Using the Single-photon Absorption Process The single-photon absorption process represents the case where the wavelength of the laser is in direct agreement with the absorption band (energy difference ΔE) for the material of interest. Upon illumination with this light, the material first starts to absorb it. If the transition energy of the material matches the wavelength of the light, resonant energy transfer to electrons can be accomplished. If a high-intensity laser field is applied such that a wavelength mismatch causes a corresponding quantity of the Stark spread to be produced, energy can be transferred to electrons after the necessary intensity is reached. If there is a shift from the resonance energy in a low-intensity laser field, energy transfer is initiated in response to a slight absorption of the tail of the Stark spread in the material.

If a large quantity of energy cannot be transferred to electrons in the material at the first stage of the process, the short-pulse laser has difficulty in achieving effective processing on account of the short pulse duration. This is why absorption of light at optimum wavelength is critical. Since the short-pulse Raman laser can utilize Raman light, various wavelengths can be chosen by selecting a suitable Raman medium.

ii) In the Case of Using the Multi-photon Absorption Process

The multi-photon absorption process is the process of absorbing two or more photons of the same origin. For the sake of convenience in explanation, let us assume the case of using an atom as a target of illumination. If the atom makes a transition from the (γJ) state to the (γ'J') state and if the transition matrix is written as D, the atom's dipole moment $\mu$ is expressed by the following equation:

$$\mu = <\gamma J|D|\gamma'J'>$$

The intensity of the electric field $\epsilon$ is given by:

$$\epsilon = (2\pi\phi/c)^{1/2}$$

where $\phi$ is the flux of photons.

The AC Stark spread $\Omega$ is written as:

$$\Omega = \epsilon^n \Sigma_1 \ldots \Sigma_n [n\mu_{1,2} \ldots \mu_{n,n-1}/(E-E_1+h\omega)\ldots(E-E_{n-1}+nh\omega)]$$

where n is the number of actual energy levels involved, and $\mu$ is the matrix of transition between n actual energy levels.

If the amount of this shift becomes comparable to the mismatch in the energy transitional value, a strong transition occurs. Such a great shift can be caused in a laser field having high intensity level of $\epsilon$. A solid involves a field-dependent Stark spread and requires more sophisticated consideration than the above-described single molecular or atomic model; however, estimation is essentially the same between the two cases.

From the above equation, one can see that excessive laser light must be used if there is a great mismatch; by choosing the resonant wavelength, a process can be realized that is efficient and will not impose any undue thermal impact on the substance of interest.

The actual substance is complex and intricately dependent on illumination and other factors. To explain analytically, let us consider the simplest case of a one-photon transition from an isolated atom. The density N of the upper energy level is expressed by:

$$N = (N_0 \; \Omega_R^2/(\Delta^2+\Omega_R^2))(1-\cos(\Delta^2+\Omega_R^2)^{1/2}t)/2$$

where $N_0$ is the total number of the photons, $\Omega_R = 2\epsilon D/h$ or Rabi frequency, $\epsilon$ is the intensity of electric field, D is dipole moment, $\Delta$ is detuning (the mismatch between the resonance energy and the laser excitation energy).

In order to increase the value of N, $\Delta$ has to be increased to a value comparable to $\Omega_R$. Conversely, if $\Delta$ is large, the laser output has to be increased to increase the Rabi frequency. With large dipole moments as in atoms, $\Omega_R$ is about 10 MHz at an illumination intensity of about 1 W/cm². Conventional lasers emit intensities of GW/cm² whereas the short-pulse Raman laser of the present invention emits an intensity of the TW/cm² order. In other words, the Rabi frequency at the intensity of the conventional lasers is about 100 GHz whereas the short-pulse Raman laser has a Rabi frequency of about 100 THz. This means that the short-pulse Raman laser has a greater chance of causing multi-photon transition. The relative occurrence of this transition is roughly calculated below using the coefficient $\Omega_R^2/(\Delta^2+\Omega_R^2)$ and compared with experimetal values.

Assume the processing of glass having the spectrum shown in FIG. 2. A conventional laser (YAG laser) emits at a wavelength of 1060 nm and the short-pulse Raman laser to be used in the invention emits at a wavelength of 1200 nm. The gap energy is approximately 4 eV (≈300 nm). In the conventional laser, three photons are sufficient to gain a value near the gap energy, so the detuning $\Delta$ is calculated as follows: 300 nm–1060 nm/3=1000 THz–852 THz=148 THz. In the short-pulse Raman laser, Δ=300 nm–1200 nm/4=0 (resonance). This is the condition for resonance to occur in the multi-photon transition process.

Hence, the value of $\Omega_R^2/(\Delta^2+\Omega_R^2)$ is very small (4.5×10⁻⁶) with the conventional laser but approximates unity with the short-pulse Raman laser. These are theoretical values calculated for maximum intensity and when the laser produces low output in the initial pulse period, the difference becomes greater. Thus, the oscillating wavelength of the short-pulse Raman laser coincides with the multi-photon absorption wavelength and its laser intensity is high; as a result, even four photons which are less efficient than the three photons emitted from the conventional laser can instantaneously be excited 100% to the upper energy level.

iii) Changing the Raman Laser Wavelength and the Shortest Pulse Duration

The Raman laser wavelength and the pulse duration can be altered by using Raman crystals made of the Raman materials listed in Table 1.

3) System Examples

Processing by illumination with the short-pulse Raman laser requires an intensity of the TW/cm² order and it is necessary to adjust this value to the specific substance to be processed or measured in industry. A suitable configuration of the short-pulse Raman laser is shown in FIG. 3.

The system of the present invention permits the use of a pump laser having various pulse durations and wavelengths. A chosen Raman medium is illuminated with this pump laser to generate a first-stage short-pulse Raman laser having the fundamental wave and the first through fourth harmonics at various wavelengths (with pulse durations of 20–40 ps). A chosen Raman medium is illuminated with this first-stage laser to generate a second-stage short-pulse Raman laser having the fundamental wave and the first through fourth harmonics at various wavelengths (with pulse durations of 1–4 ps).

BRIEF DESCRIPTION OF THE DRAWINGS

The patent or patent application file contains at least one drawing executed in color. Copies of this patent or patent application publication with color drawing(s) will be provided by the Office upon request and payment of the necessary fee.

FIG. 3 shows the configuration of an industrially applicable short-pulse Raman laser;

FIGS. 5A and 5B are a set of optical micrographs showing the result of condensing short-pulse laser within glass to work only its interior without affecting the surface.

DETAILED DESCRIPTION OF THE INVENTION

Figure 1:
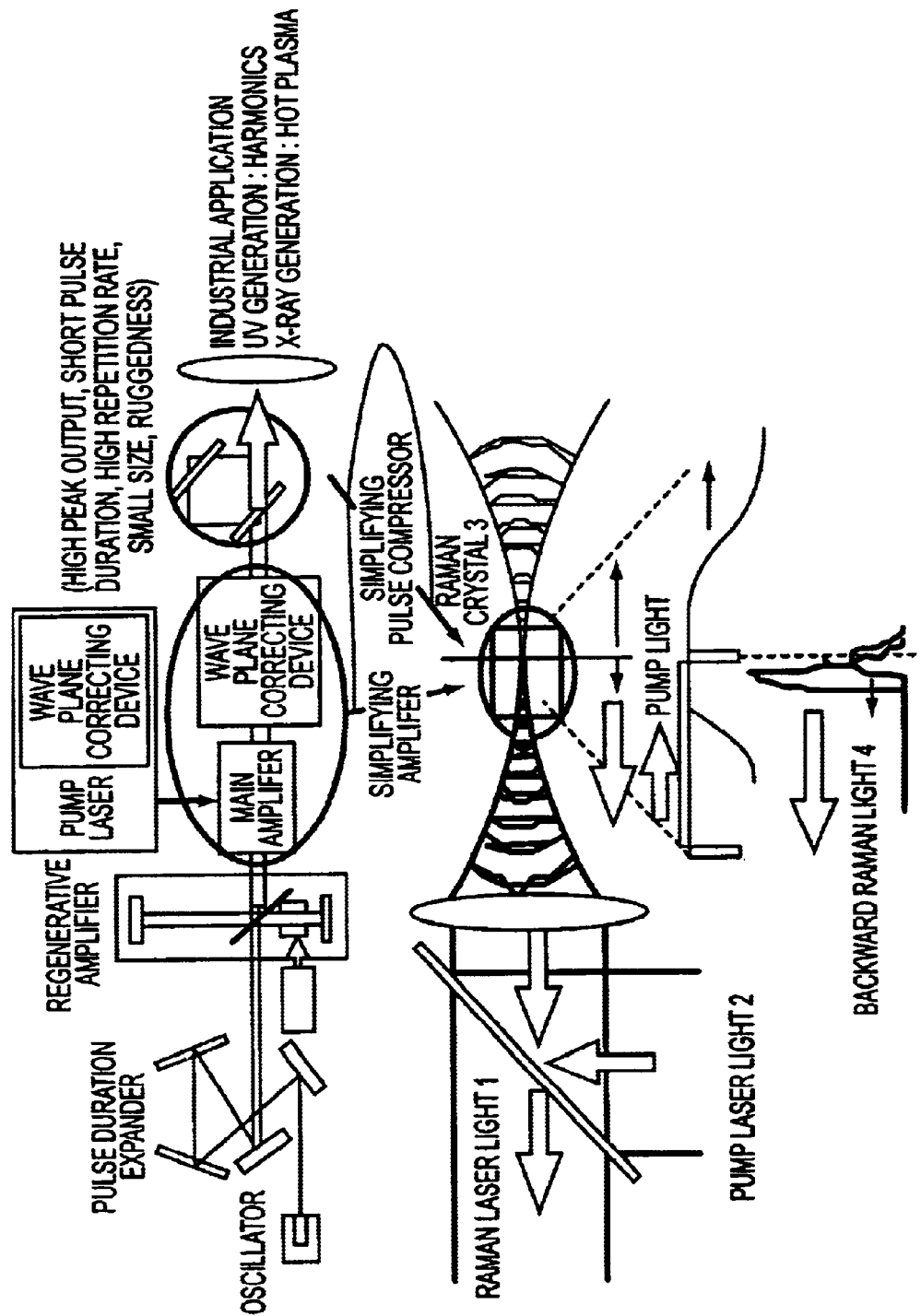
FIG. 1 shows the theory of oscillating short-pulse Raman laser light [in glass working, calcite ($CaCO_3$) was used as a Raman crystal to generate light at 1.203 μm with a pulse duration of 20 ps in response to pump light at 1.06 μm]
Figure 2:
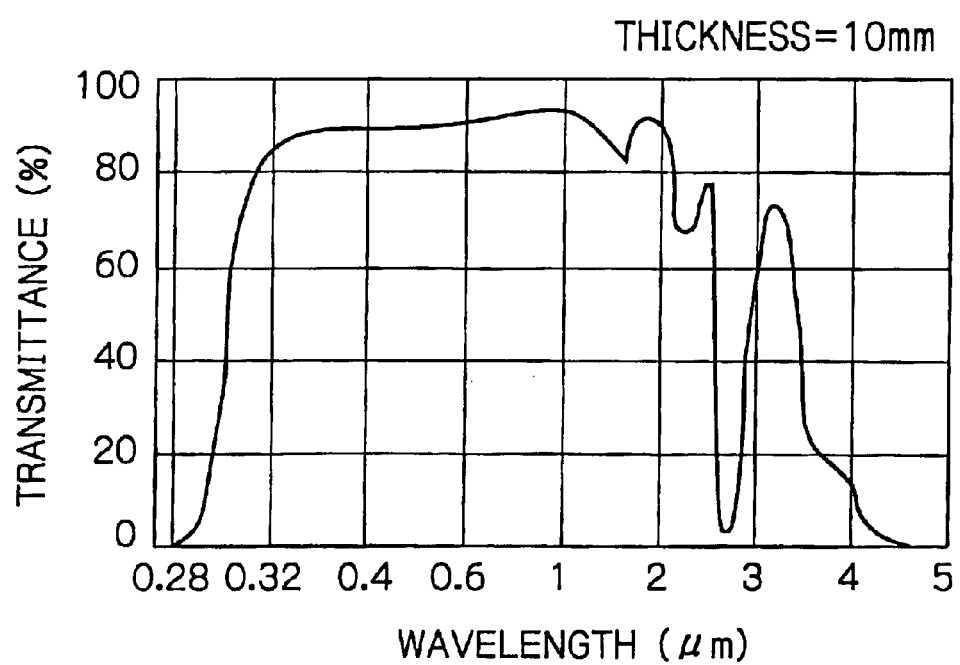
FIG. 2 shows the transmittance of the glass used in the working experiment.
Figure 4A:
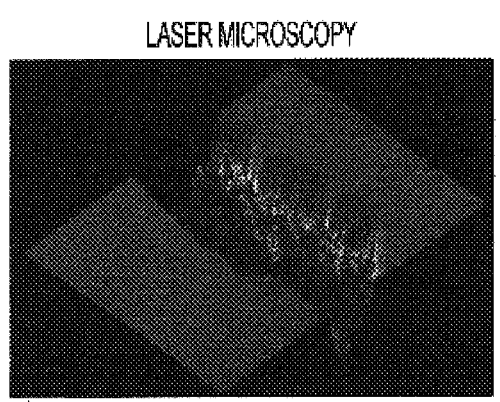
FIGS. 4A–4D are a set of micrographs showing the surfaces of glass sheets processed with long-pulse laser and short-pulse laser.
Figure 4B:
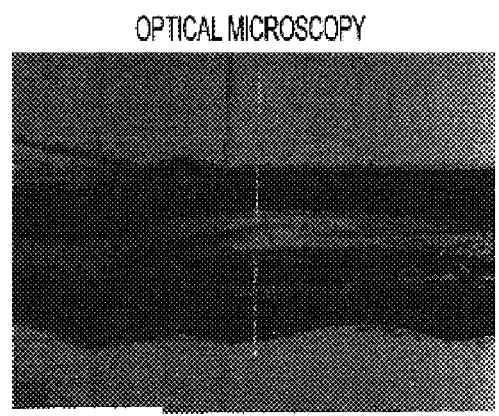
Figure 4C:
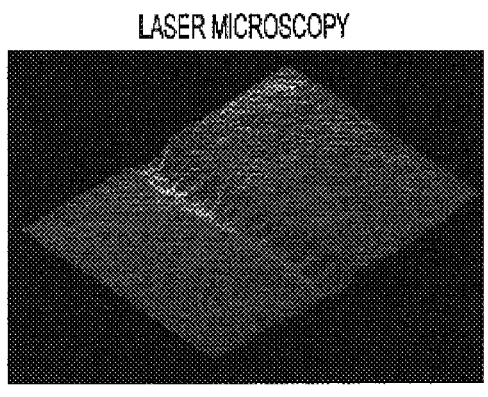
Figure 4D:
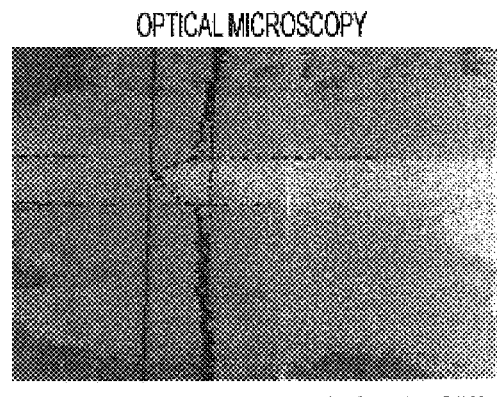

The performance of laser processing depends on various parameters such as laser output, modulation (how to apply pulses), wavelength, and beam quality (which influences light convergence) and many laser processing techniques have been implemented by manipulating these parameters.

Speaking of laser pulses that are applied to working operations such as drilling and cutting, if the laser pulse duration is long, the plasma generated from the material illuminated with the leading edges of pulses interacts with the trailing edges of the same pulses and makes no contribution to working; in addition, the plasma is heated and interacts with the material to damage the work.

In an even earlier stage of processing, the energy of the laser is first absorbed by an electron, then transferred to the surrounding lattice, and propagates in the form of heat. If the processing step ends before energy is transferred to the lattice, no adverse thermal effects such as cracking will occur to the work.

This is how it became desirable to develop the technology of processing with short pulses. Evolution of this technology will hopefully lead to the development of a method in which the coulomb force created in a substance illuminated with high-intensity light produces a strong enough breaking force to cause instantaneous ablation of the substance.

To perform this desirable processing, short pulses and an intensity of at least TW/cm² are required and this in turn requires a beam of such high quality that the output laser light can be converged to a small enough spot. If these effects are generated by the multi-photon absorption process, the interior of a transparent material can selectively be processed. Consider a substance that transmits incident light; by allowing the incident light to focus within the substance, the many-photon effect enables electronic energy to be transferred to the neighborhood of the focal point, thus

TABLE 1

| Raman material | Shift (1/cm) | Line width (1/cm) | Gain coefficient (cm/GW) | Phonon life (ps) | Surface damage threshold (GW/cm²) | State | State |
| --- | --- | --- | --- | --- | --- | --- | --- |
| Ba(NO3) 2 | 1048.6 | 0.4 | 10 | 25 | 2.5(lns) | solid | solid |
| NaNO3 | 1069.2 |  | 7.0 | 10 |  | solid | solid |
| CaCO3 | 1086.4 | 1.2 | 1.6 | 8.3 | 10(lns) | solid | solid |
| KGd(WO4) 2 | 901 | 5.4 | 3.8 | 1.9 |  | solid | solid |
|  | 768 | 6.4 | 4.4 | 1.6 |  |  |  |
|  | 757 |  | 1.0 | 0.7 |  |  |  |
| LiNbO3 | 256 | 23 | 8.9(2) | 0.4 | 2.5 | solid | solid |
|  | 637 | 20 | 9.4 |  |  |  |  |
| LiTaO3 | 201 | 22 | 4.4 |  |  | solid | solid |
| H2(50atm) | 4155 |  | 1.0 | 70 |  | gas | gas | making it possible to perform selective working of the interior of the substance.

By the same method, light incident on the surface of the material is allowed to go deeper in the interior, given energy in situ from many photons and observed by either visible or ultraviolet light. The light emitting from within the material is picked up to examine its interior. Specific applications of this technique are described below.

(1) Realizing a Precision Processing Method that Causes No Thermal Effect on the Work The conventional processing with short pulses has no laser light available that matches the wavelength of absorption by the material and the only method that can be employed is absorption by means of the Stark spread that is created by a high-intensity laser field. In this method, short pulses are not effectively used since their leading edges are simply lost. In addition, reflection causes interaction with the ambient gas atmosphere to cause breakdown and other adverse effects on the surface of the work. As a further problem, in order to create a strong Stark effect, the laser light has to have more-than-necessary intensity; this not only requires a large laser but also imparts more-than-necessary energy to electrons, making it impossible to achieve high-precision processing while reducing the processing efficiency.

Highly efficient and precise processing can be realized by using short-pulse laser light that has material-matching absorption wavelength (or many-photon absorption wavelength). This technology is especially desired by the semiconductor industry to perform super-microfabrication.

(2) Processing and Measuring the Bulk State

If laser having a wavelength that is hardly absorbed by the material is condensed to be focused in the interior of the material, multi-photon absorption occurs in the area where the laser is focused and that area is excited to a higher energy state. If the wavelength of the laser light matches the multi-photon absorption wavelength, even weak light is sufficient to cause multi-photon absorption. If the interior of the material is to be subjected to fine processing, too intense laser light causes adverse effects. In diagnosing the living body, fluorescence or other emission that comes from within the material on account of multi-photon excitation is employed and in this case, the occurrence of ionization and ablation must be avoided. To use weak light and still obtain sufficient fluorescence, it is necessary to use the multi-photon absorption wavelength.

This technology holds promise as a medical technique for examining the interior of the skin and as a technique for processing the interior of transparent materials such as glass.

(3) Specific Applications

1) Industrial Application Making Use of Processing with Small Thermal Impact

Two typical examples are the processing of semiconductor micro-packages and the processing of ceramic ferrules used in optical connectors and these are specifically described below.

Machining involves the development of extensive micro-cracking. The conventional laser working with long-pulse laser causes significant effects on the work due not only to heat but also to flown chips. There are two points to consider for successful achievement of this processing technology; one is to minimize the optical input to reduce thermal effects and the other is to improve the working efficiency. To minimize the optical input, it is necessary to use laser light at a wavelength that matches the wavelength of absorption by the material. To improve the working efficiency, it is necessary to use pulses of the required duration which are the longest on the condition that they comply with the thermal characteristics of the material of interest.

However, none of the conventional short-pulse lasers have sufficiently high energy to achieve the desired processing and still are tunable in wavelength. It has also been difficult to adjust the pulse duration to a desired value.

The Raman short-pulse amplifying laser under discussion is such that the emission wavelength matching the wavelength of absorption by the substance of interest can be realized in an easy and compact way by choosing a suitable Raman medium, adjusting the wavelength of the Raman pump laser, using harmonics of Raman light, etc. By adjusting the method of condensing light in the Raman medium, the region for the occurrence of the Raman effect can be controlled and this in turn enables alteration of the pulse duration.

2) Medical Application Making Use of the Many-photon Absorption Process with Small Thermal Impact The development of laser-based technology contributes to non-invasive diagnoses and treatments in the medical field. The use of short-pulses expands the applicability of lasers to in situ examination and painless processing of tissues, as described below.

Medical testing of tissues, for example, dental checkup of caries and pyorrhea alveolaris is currently performed either visually or by radiography. In visual testing, only the surface of the tissue can be seen and what is more, visual testing provides only rough evaluation and even specialists have considerable difficulty in finding out changes in details of the tissue. In addition, the conventional dental radiography which uses an external X-ray source requires a long enough shooting time to pose the problem of radiation exposure. As a further problem, the low resolution of radiography presents difficulty in having exact knowledge about the progress of root caries.

To perform diagnosis while imposing the least possible burden on the patient, it is necessary to use a laser emitting at a wavelength that matches the wavelength band of absorption by the tissue of interest. Conventional techniques such as laser fluoroscopy are interfered with by ubiquitous in vivo compounds such as porphyrins and difficulty is encountered in observing the condition of the tissue itself. Under these circumstances, the many-photon absorption process is used to eliminate the interference by undesirable compounds and acquire clear information. The information must reflect not only the surface of the tissue but also the subsurface area.

To meet these requirements, short-pulse light is chosen that is not directly absorbed by the tissue (due to long wavelength) but which produces multi-photon process that match the absorption wavelength and such short-pulse light is condensed at a sub-surface site to be examined. The light has long enough wavelength to be launched into the tissue and, upon reaching the focal point, it produces fluorescence or other emission by the multi-photon absorption process. By using the resultant information as database for tissue examination, positive medical checkup can be realized.

If a single photon or multi photons are allowed to match the absorption wavelength, less photon energy is needed to process tissues and the short pulse duration enables painless processing. This technology forms an important part of medical and cosmetic industries by enabling various operations such as the removal of dental scale, sterilization of dermatophytes that infest the skin such as dermis, depilation, implantation of hair, and removal of corneum.

The following examples are provided for the purpose of further illustrating the present invention.

EXAMPLE 1

Working Glass Surface

To show the difference between a conventional YAG laser (pulse duration, 10 nanoseconds; wavelength, 1.06 $\mu$m) and a short-pulse Raman laser (pulse duration, 30 picoseconds; wavelength, 1.2 μm), the surface of glass was worked over a width of 30 μm. As already mentioned, the conventional laser is non-resonant even with three photons whereas the short-pulse Raman laser of the invention is essentially resonant with four photons and hence supplies lower energy to the glass to be worked. As shown in FIGS. 4A–4D, working with the short-pulse Raman laser caused extremely small thermal effects such as cracks, as compared with working by the YAG laser of longer pulse duration.

EXAMPLE 2

Working the Interior of Glass

This example shows the case where light having a wavelength that is capable of transmission through glass is condensed in its interior to create the many-photon effect only in the area where the incident light is focused, thereby enabling selective working of the interior of the glass without affecting the surface at all. Since the light confined in the interior of the glass is capable of effective processing, the internal processing (see FIG. 5B) was more pronounced than the surface processing (see FIG. 5A).

EXAMPLE 3

Concentrated Heat Absorption vs. Heat Diffusion as They Affect Processing

Figure 6A:
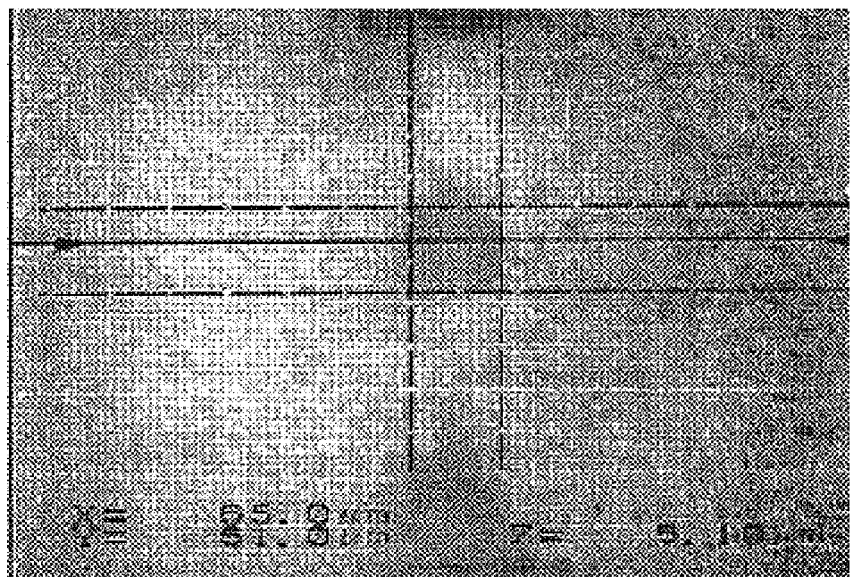
FIGS. 6A and 6B compare the size of marks left on glass by processing through laser illumination with the size of marks left on silicon.
Figure 6B:
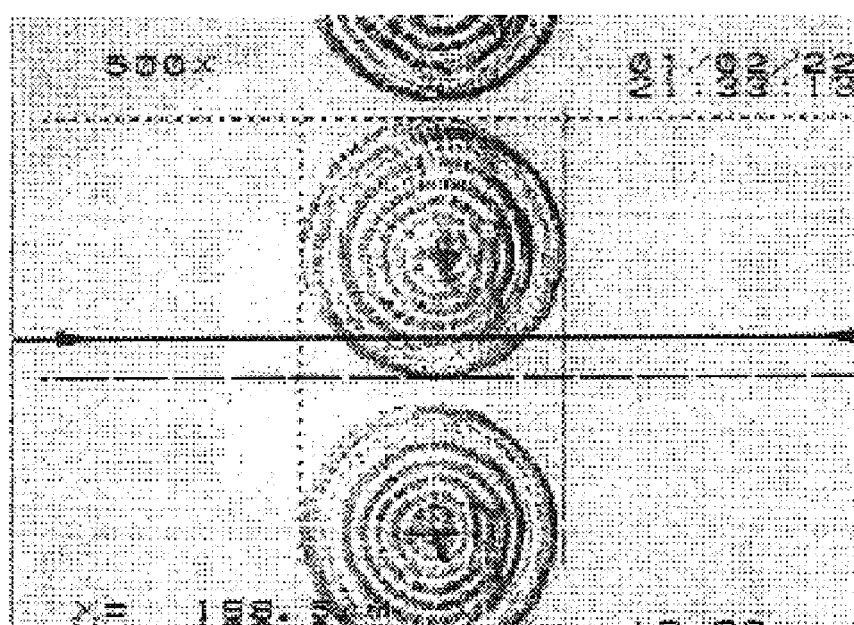

As FIGS. 6A–6B show, glass and silicon are processed in greatly differing sizes when they are illuminated with laser under the same conditions. Upon examination by laser microscopy, the marking left on the glass by processing is not highly visible; as already mentioned, the input of light energy into the glass was concentrated on account of a virtual many-photon absorption process, so the processing size was near the spot size of the laser beam used.

On the other hand, silicon is offset from many-photon resonance and heat absorption does not occur in a concentrated way; in addition, there were so many free electrons as in metals that the surface electrons accelerated by the electric field of the laser exerted thermal effects on the surrounding area. As a result, the marking left on silicon was three times as large as the marking left on the glass.

The present invention offers the following two characteristic advantages: first, by using a short-pulse Raman laser, processing or measurement can be performed without causing thermal effects on the work; second, by using a short-pulse Raman laser having a wavelength that is hardly absorbed by a material, the interior of the material can be processed or measured without damage.

What is claimed is:

1. A method for achieving a high-density concentration of laser light from a short-pulse Raman laser light capable of generating a sufficiently broad wavelength and pulse duration to match optical absorption characteristics of a substance having a single-photon absorption wavelength, said concentration sufficient to process or measure the substance at a speed higher than the speed at which thermal effects propagate in the substance to prevent thermal or mechanical deterioration of the surface of the substance, said method comprising adjusting at least one of spatial light convergence, temporal light convergence, and the wavelength of the light to process or measure the substance, wherein flat waveplanes are produced by ensuring that the Raman laser has the same thermal effect on a crystal for a Raman medium as on a conventional laser medium, or by generation of higher order non-linear effects in an area of high optical density, and to yield a high intensity of light convergence and to achieve said spatial convergence;

wherein the pulse duration of the light is varied in the range ofpico- to sub-pico-seconds by changing the convergence shape of the light from the pump laser or by changing the shape of the crystal to achieve temporal light convergence; and tuning the wavelength of the light by selecting an appropriate crystal for the Raman medium that emits light at the desired wavelength or by changing the wavelength of a Raman driving light source or a Rarnan pump laser light.

2. The method of claim 1, wherein the substance has a multi-photon absorption wavelength, said method further comprising, determining that processing or measuring at the single-photon absorption wavelength was not effective, and adjusting the light from a high peak-output laser having the resonance energy of the substance to the multi-photon absorption wavelength of the substance and condensing the high-output light with the laser light to boost the laser light and enable injection of the laser light energy into the substance at higher efficiency than non-boosted injection.

3. The method of claim 1, wherein the substance has a multi-photon absorption wavelength, said method further comprising, processing or measuring an area of the substrate equal to the area of that portion of a multi-photon pulse of laser light having a high-intensity central cross-sectional area comprising a higher concentration of multi-photon effect than the remainder of the cross-sectional area, said substrate area being smaller than the cross-sectional area of the laser beam, to provide finer processing.

4. The method of claim 1, wherein the substance has a multi-photon absorption wavelength, said method further comprising, precisely and selectively processing or measuring a small volume in the interior of the substance determined by the cross-sectional area of the beam in the direction perpendicular to the beam and the duration of the pulse in the direction parallel to the direction of travel, wherein the Raman laser light has a long wavelength in the infrared range and is used to condense the Raman light and focus it in the interior of the substance where it performs the processing or the measuring with light in the visible to ultra-violet range.

5. The method of claimed 4 herein the visible to ultra-violet light is generated in a volume deep in the substance and is used to process or measure the subsurface volume of the substance that cannot be directly observed from the surface.

* * * * *

UNITED STATES PATENT AND TRADEMARK OFFICE
CERTIFICATE OF CORRECTION

PATENT NO. : 6,906,283 B2
DATED : June 14, 2005
INVENTOR(S) : Takashi Arisawa et al.

It is certified that error appears in the above-identified patent and that said Letters Patent is hereby corrected as shown below:

Column 12,
Line 11, replace "ofpico-" with -- of pico- --.
Line 18, replace "Rarnan" with -- Raman --.

Signed and Sealed this

Twenty-first Day of March, 2006

JON W. DUDAS
*Director of the United States Patent and Trademark Office*